US00PP18455P3

(12) United States Plant Patent
White

(10) Patent No.: US PP18,455 P3
(45) Date of Patent: Jan. 22, 2008

(54) MINI-FLORA ROSE PLANT NAMED 'SAVAMOON'

(50) Latin Name: *Rosa hybrida*
Varietal Denomination: SAVamoon

(75) Inventor: Wendy White, Ipswich, MA (US)

(73) Assignee: Nor'East Miniature Roses, Arroyo Grande, CA (US)

( * ) Notice: Subject to any disclaimer, the term of this patent is extended or adjusted under 35 U.S.C. 154(b) by 28 days.

(21) Appl. No.: 11/301,172

(22) Filed: Dec. 12, 2005

(65) Prior Publication Data

US 2007/0136901 P1 Jun. 14, 2007

(51) Int. Cl.
*A01H 5/00* (2006.01)

(52) U.S. Cl. ..... Plt./117

(58) Field of Classification Search ..... Plt./116, Plt./117
See application file for complete search history.

(56) References Cited

PUBLICATIONS

Internet website "HelpMeFind"; Roses; 'Savamoon'; www.helpmefind.com/rose/pl.php?n=45009.(1 page total).*

* cited by examiner

*Primary Examiner*—Kent Bell
*Assistant Examiner*—S. B. McCormick-Ewoldt

(57) ABSTRACT

'SAVamoon' is a new and distinct variety of mini-flora rose plant with a very pale violet-lavender to near white, fully double flower having a very strong fragrance. Blooms are borne primarily singly and serve well as cut flowers. There is little change in the color of the petals as the flower opens and ages. 'SAVamoon' serves well as a perennial or large container plant.

1 Drawing Sheet

Genus and species: *Rosa hybrida.*
Varietal denomination: 'SAVamoon'.

CROSS REFERENCE

There are no other roses from this hybridizing program that bare resemblance to this new cultivar as a new rose was brought in for the cross that created 'SAVamoon'. Although there are other white or near white roses from this breeding program, there are none with this size bloom, petal count, strong fragrance or plant size. There are other strongly fragrant roses in this breeding program, but none of this plant habit or color. The closest related roses are those having 'MACgenev' (U.S. Plant Pat. No. 8,279) as their pollen parent as this is a grandparent in this new invention. In this regard, a cultivar recently introduced from this breeding program, 'SAVapam' (U.S. Plant Pat. No. 17,329), would bear the closest resemblance to this new cultivar in flower form and size of open bloom and with similar foliage size. The fragrance of 'SAVapam' is moderate and the color is a medium pink and pink blend.

BACKGROUND OF THE INVENTION

This present invention relates to a new and distinct variety of hardy, bush type rose plant of the mini-flora class. This new variety was created by myself under controlled conditions in a greenhouse in Rowley, Mass., in 1998, by crossing 'SEArodney', not patented, as seed parent, and unnamed, an unintroduced seedling created by this same breeding program, as pollen parent.

The goal of making this cross was to produce a fragrant miniature rose. To achieve this, the parents were chosen for their size, both being minis, and their strong fragrance. This resulting rose, the only seedling selected from this cross, is extremely fragrant. The size of the bush and flower are large for a miniature but of a good size for the mini-flora class.

This new invention bares similarities to its seed parent, 'SEArodney'. Both have near white flowers averaging three inches in diameter, with a strong, fruity fragrance. This new invention has a plant that is a little more compact; more vigorous; grows 12 to 18 inches taller, up to 32 to 40 inches tall; and having a flower with more petals than 'SEArodney'. The color of flowers on 'SEArodney' is light pink to near white. The flowers on the new invention are a very pale violet, more often appearing white.

The differences between the new invention and the pollen parent are many. The pollen parent is also fragrant but its flowers are not more than 2 inches in diameter and have considerably fewer petals. The plant habit of the pollen parent is narrow-upright and only grows 24 to 30 inches tall.

Asexual reproduction by cuttings of this new cultivar in Rowley, Mass. and Arroyo Grande, Calif. shows that all distinguishing characteristics of this rose continually come true to form.

SUMMARY OF THE INVENTION

The present invention relates to a new and distinct variety of hardy, bush type rose. The characteristics distinguishing it from all other similar varieties of which I am aware are its unique combination of fast repeat flowering habit; the 2½ to 2¾ inch size of open bloom; its usually high petal count, having well over 40 petals on the first spring blooms; its very strong and fruity fragrance and the relatively small size of its individual leaflets.

The new invention is further characterized by

These fully double and fragrant flowers borne singly;

Flowers that hold up well when cut, emitting their strong fragrance;

Dull, medium to dark green foliage;

Upright and well branched growth habit, growing 36 to 40 inches tall;

Suitability for production from softwood cuttings in pots;

A plant that grows and blooms amazingly in the greenhouse and satisfactorily outdoors, providing decoration and outstanding fragrance in the garden as a perennial or in large containers.

BRIEF DESCRIPTION OF THE DRAWING

The accompanying drawing is of three photographs:

The bottom image was taken in August in San Luis Obispo County, Calif. The larger of the images on the upper portion of the page was taken in September of blooms cut from plants grown under plastic in Essex County, Mass., and the smaller inset image, to show the peduncles and the different colors found on the opening bud, was taken in November from a plant grown outside in Essex County, Mass.

BOTANICAL DESCRIPTION OF THE PLANT

The following observations, measurements, values and comparisons describe 5 to 6 year old plants of *Rosa hybrida* 'SAVamoon', grown in artificial soil mix in three and five gallon plastic nursery containers in Ipswich, Mass., except where otherwise noted. Color References are made using The Royal Horticultural Society (London, England) Colour Chart, except where common terms of color are used.

Genus: *Rosa hybrida.*
Species: 'SAVamoon'.
Market class: Mini-flora.
Seed parent: 'SEArodney'.
Pollen parent: An unnamed, unintroduced seedling of Jean Kenneally (U.S. Plant Pat. No. 5,637) by 'MACgenev' (U.S. Plant Pat. No. 8,279).
Flowers:
*Blooming habit.*— Repeat bloomer with flowers borne mostly singly on straight stems of medium strength.
Bud: Form is broadly ovoid with an acute apex. The size just before the sepals divide varies from 11/32 to 14/32 inch and length varies from 7/16 to 10/16 inch.

Colors that appear on the reverse of the petals when the sepals first divide may be a very pale green, near 145C from the Yellow-Green Group, or near 155A, from the White Group, or a combination of the two colors and often with areas of a color, either a medium red-purple, near 74A, or a more pink, near 67C, also from the Red-Purple Group.

Sepals: There are 5 sepals. On occasion, 2 adjacent sepals may be found to be entirely congenitally joined along one side having an extended base with a width of 9/16 inch and length of 9/16 to 11/16 inch to a single tip. Occasionally there will be a foliar appendage extending from the center of this conjoined sepal. The longest outer sepal extends beyond the tip of the bud by 3/16 to 9/16 inch. The color of the outer surface of those sepals on the sunward side is a dark yellow-green, near 146A, flushed lightly with a deep grayed-purple, near 187A, and a Lettuce Green, near 144A at the base. The color of the outer surface of those sepals away from the sun is near 144A and also lighter at the base, near 144C, and some areas flushed with near 187B. The inside surface of all sepals is a dark yellow-green, near 147B, and are tomentose, making it appear flushed with white.

The two outer sepals are a narrow deltoid shape with an acuminate apex. The other three sepals are an ovato-oblong shape with an acuminate apex. Connate sepals are of the later group and have a very broad deltoid shape. All sepals have ciliate margins. The sepals roll back with the petals until they are perpendicular to the stem.

The two outermost sepals have one to three foliar appendages of varying sizes along each margin. When the flower is half open these outer sepals measure about 3/4 inch long and 4/16 to 5/16 inch wide with a peniculate tip 5/32 inch long.

The two innermost sepals have no foliar appendages. The width is usually 1/4 inch but they are of unequal lengths, varying from 23/32 and 24/32 to 21/32 and 23/32 inch long. They have a sharply acuminate tip of 5/32 to 6/32 inch long.

The one sepal in-between the inner and outer has foliar appendages only along one margin and a sharply acuminate tip of about 5/32 inch long.

Blooms measure 2½ to 2¾ inches across when full open. Petal count can vary from 26 with 3 petaloids to 63 with 8 petaloids, with the highest petal counts from plants grown in Essex County, Mass., USDA zone 6, and the lesser in Arroyo Grande, Calif., USDA zone 8. Usual counts vary from 36 petals with 3 to 6 petaloids to 47 petals with 8 petaloids. Fragrance is very strong and fruity. The flower remains fresh on the plant for 7 to 9 days and equally as long or longer as cut flowers. The upper profile remains flat from open to fade. The lower profile progresses from cupped to flattened convex.

Petals have a smooth and satiny upper and lower surface. The shape of the outer petals is obcordate. Their base is obtuse and the outer margin is crenate. The intermediate petals are obovate with entire margins, occasionally having an acute apex and inner petals are ovato-oblong with an emarginated apex, occasionally having an acute tip on one side of the notch. The outermost petals measure from 1⅛ to 1¼ inches wide and 1¼ to 1½ inches long. Their arrangement is imbricated.

From plants grown outside in Essex County, Mass., the closest color of the upper surface of the petals, on a newly opened bloom in November, is near 155D from the white group. The basal area and point of attachment are a very light greenish-yellow, near 2A. The reverse of the petals is closest to 155B with a basal area of a very light Sulphur Yellow, near 6D, and a very light yellow-green, near 154D, at the point of attachment.

When half blown, the color of the upper surface of outer petals remains unchanged. The reverse of the outer petals is between 85D and 158D, particularly around the outer margins and then becoming a light Barium Yellow, near 10D, into the basal area and a little darker, near 10C, at attachment. The inner petals become a very pale Sea Lavender Violet, nearest 85D. The basal area becomes a medium Mimosa Yellow, near 8C and the point of attachment is a little darker, near 8B. The reverse is lighter than the upper surface and with more yellow tones, a color lighter than between 85D and 8D. Basil area and point of attachment is a medium Mimosa Yellow between 8B and 8C.

From plants grown inside under plastic in San Luis Obispo County, Calif., the color of the upper surface of the petals is lighter than a color near 76D, a pale shade of lilac, along the outer edges. The basal area and point of attachment is near 8B, a medium shade of Mimosa Yellow. The two colors are combined throughout the remainder and majority of the petal surface to become a color near 161D, a light tan. The reverse of the petals begins as a medium Mimosa Yellow, near 8B, at the base and point of attachment and lightens as it proceeds up the petal, first to a color between 8C and 159D from the Orange-White Group, and finally to a color between 8D and 159D.

As the bloom ages, the amount and degree of yellow in the petals decreases, leaving the petals appearing lighter than a color between 159D, 84D, Mineral Violet, and a very light gray, near 202D. Only the basal area shows yellow, a very light Primrose Yellow, nearest 4D, on both surfaces of all petals. The color at the points of attachment is a little darker, nearest 4C.

General tonality of the flowers of this new cultivar when grown outside in October and November in Essex County, Mass., is a slightly off-white and when grown under plastic in Essex County, Mass. or San Luis Obispo County, Calif., is a very light lilac. Tonality from a distance is white.

Petaloids tend to be misshapen and partial petals. They otherwise have the same characteristics and coloring of the inner petals.

The receptacle has a cuneate profile, varying from 7/32 to 9/32 inch in diameter and having a height of from 9/32 to 11/32 inch. The color is near 146B, a medium yellow-green and may appear flushed lightly on the sunward side because of the numerous stipitate glands that are tipped with a color near 187B, from the Greyed-Purple Group. The surface is matte and has numerous prickles as well as the stipitate glands. The top surface is usually circular with a diameter between 4/16 and 5/16 inch. Occasionally it may be oval with diameters of 10/32 inch by 11/32 inch. The surface is glabrous and the color is a very light Mimosa Yellow, near 8D. Long, upright hairs protrude from the alveola in the center of the top, surrounding the styles as a group.

Peduncles are of medium strength and straight. Lengths vary from 1⅝ to 2¼ inches. Diameter is most often 3/32 inch but may be as large as ⅛ inch. The length of the peduncle does not correlate with the diameter. The surface is glossy near the receptacle and semi-glossy where it connects to the stem. The color is a medium yellow-green, near 146A, and when young is flushed with a color nearest 180A, from the Greyed-Red Group. There are a few miniscule prickles, some hairs and many stipitate glands. Stipitate glands are tipped with a color near 180D. There are foliar appendages in pairs at the base of the peduncle. These were found to be sepalous on plants grown in Massachusetts. These sepalous appendages have many stipitate glands of varying lengths but nearly evenly spaced along the margins and many hairs near the apex. At the base of the peduncle in Arroyo Grande, Calif., the appendages are more apt to be leaves with only one to three leaflets.

Reproductive organs: Stamens, filaments and anthers are arranged regularly around the styles, attached to the outer rim of the receptacle. Quantity is between 47 and 71, the most common amount is 65 to 67. On the half opened flower the length of the filaments ranges from 3/16 inch to 5/16 inch. By the time the flower is full blown the length is around ⅝ inch. The color of the filaments in the half opened bloom is light green-yellow, between 2D and 1D. When the flower is full open, this color has become dull, between161D and 162D, from the Greyed-Yellow Group. The color of the anthers is Saffron Yellow, near 19B. On the full open bloom the color of the pollen sacs surrounding the anther is near 162B on the plants grown outside in Massachusetts and near 167B, from the Greyed-Orange Group, on the plants grown under plastic, which also have with the more intense flower color. Pollen color is near 169C on the plants grown under plastic. When the pollen from the plants grown outside in Massachusetts dries, it is a color between 163A and 167A from the Greyed-Orange Group. The anthers yield a small amount of pollen.

*Pistils, styles and stigmas.*— The quantity of the pistils is near the same as the quantity of stamens. The color of the styles is the same on plants grown in all locals, a very light Mimosa Yellow, near 8D, at the base and near 160C, from the Greyed-Yellow Group, near the top. The length varies from 3/16 to 5/16 inch. The color of the stigmas is the same as the upper part of the styles.

Hips tend to be elliptical to oval in shape with diameters of about 11/16 inch by 10/16 inch and having a height of 11/16. There are no mature hips to observe at the time of the writing of this application.

Plant: The plant of this new invention is uniformly branched and upright growing to a height of 36 to 42 inches and a width of 28 to 40 inches. New canes originate from the roots below the ground. A mature cane has a diameter of up to ⅜ inch. A new cane, originating from beneath the soil surface has a diameter of about 9/64 inch. Canes may reach up 30 inches or more before terminating with a fluorescence, often of three flowers. Laterals will initiate, indeterminately, from nodes and grow to varying lengths before terminating in a single flower. On a mature cane, nodes are generally spaced more than 2 inches apart, but being as short as 1⅞ inches and as long as 2 13/16 inches, following no pattern. On new shoots originating below the ground surface, the spacing of the nodes is well below 2 inches, ranging from ⅝ inch to 1¼ inches.

Flowering stems also vary considerably in length, most commonly varying from 3½ inches to 7 inches. When originating as a primary lateral they vary in length from 9½ inches to 14 inches. When in an inflorescence at the end of a main cane the length of the flowering stem is usually 1 to 1½ inches. The spacing for the nodes on the flowering stem is also erratic and usually less than 1½ inches, generally ranging from ¾ inch to 1⅜ inches.

The color of the new stems is dark green, near a color between 137A and 137B and may be flushed very lightly with a grayed-purple. The color of the old wood is more of a medium yellow-green, near 146B. Lenticels may begin forming on the main stalks in the first year of the plants growth. The color of the lenticular area on younger canes is near 177B, a medium shade of brown from the Greyed-Orange Group, and a grayed-green, darker than 197A, on the older canes.

Leaves are pinnately compound with seven and five leaflets, the largest quantity is seven leaflet leaves, occasionally with three leaflets and rarely with a simple leaf or two leaflets. The length of a mature seven-leaflet leaf is up to 4 1/16 inches and of a five-leaflet leaf is around 3 3/16 inches. The shape of the leaflets is ovate with an acuminate apex and oval base. The mature terminal leaflet measures between ⅞ and 1 inch wide and 1½ to 1⅝ inches long. Both leaf surfaces are matte. The main vein protrudes completely on the underside of the leaflets and the primary lateral veins protrude somewhat. The upper surface appears glabrous and the underside is leathery. The serration of the margins is fine and simple and mostly even, with a gland at the tip of most serrates. The color of the new foliage has strong anthocyanin coloration present. The upper surface is a dark green, near 137A, flushed with near 187A from the Greyed-Purple Group. The under surface is lighter, near 138A flushed with near 187C, and the main veins are between 185B and 185C. The anthocyanin coloring is absent on older foliage. The upper surface is dark green, nearest 139A, and the under surface is much lighter green, between 138B and 148C, and the main veins are a medium yellow-green, near 147C.

Petiole length is variable. The length on a seven-leaflet leaf is often between 11/16 and 13/16 inch, on a three-leaflet leaf is often 1 inch and on a five-leaflet leaf is around 15/16 inch. The diameter is usually 1/16 inch on all leaves. There are a few hairs and a few stipitate glands along the ridges of the adaxial side. Inside the groove is usually glabrous but may have one or two hairs. The abaxial side is glabrous. On young foliage, the color of the crest of the ridge on the adaxial side is near 187A with the rest appearing somewhat lighter, near 183D, also from the Greyed Purple Group. The abaxial surface is nearest 183A. On the old leaf the abaxial side is nearest 148B and the adaxial surface is near 148A in the groove and the crest of the ridges is near 185A, Chrysanthemum Crimson.

The surfaces and coloring of the rachis and petiolules are the same as the petioles. The length of the rachis on a seven-leaflet leaf is 1 15/16 inches and on a five-leaflet leaf it is 1¾ inches. The length of the petiolules to the terminal leaflet varies from 9/16 inch to 11/16 inch. The rest of the petiolules are about 1/16 inch long.

Stipules are paired at the base of each petiole and are attached for about two-sevenths of the length of the petiole, before angling out at about a 45-degree angle. Margins are entire with a few stipitate glands. The tip that is angled outward has more stipitate glands plus hairs, with the most hairs being at the juncture with the petiole. The color is a light yellow-green, between 147D and 148C, and the outer edges may be flushed with Chrysanthemum Crimson, a color nearest 185A.

Prickles on the main stalks are few to none for the lowest one-sixth to one-seventh of the cane, then three to four between nodes, regardless the distance between nodes, and then becomes five prickles between nodes, again regardless of the spacing. The primary laterals are similar but begin with three prickles between nodes near the base of the stem and then becoming five prickles between nodes, regardless of spacing. On the flowering stems there are around sixteen prickles on 6½ inches of stem or about three per inch of stem. They are straight and between 3/16 and 5/16 inch long on a narrow, linear base. The color is nearest between 176A and 176B, from the Greyed-Orange Group, when young. When mature the color is more brown, either near 177D, also from the Greyed-Orange Group, or may be a color between 177D and 199D from the Grey-Brown Group.

This new invention has good resistance to powdery mildew but is susceptible to blackspot. No rust or downey mildew has been observed on the plants. This new cultivar was tested hardy in United States Department of Agriculture Hardiness Zones 5 through 10, which is comparable to the American Horticultural Society heat zones 10 through 4.

It is claimed:

1. A new and distinct variety of hardy, mini-flora rose plant is claimed, substantially as illustrated and described, with fully double, very pale violet to near white flowers and having a very strong fragrance.

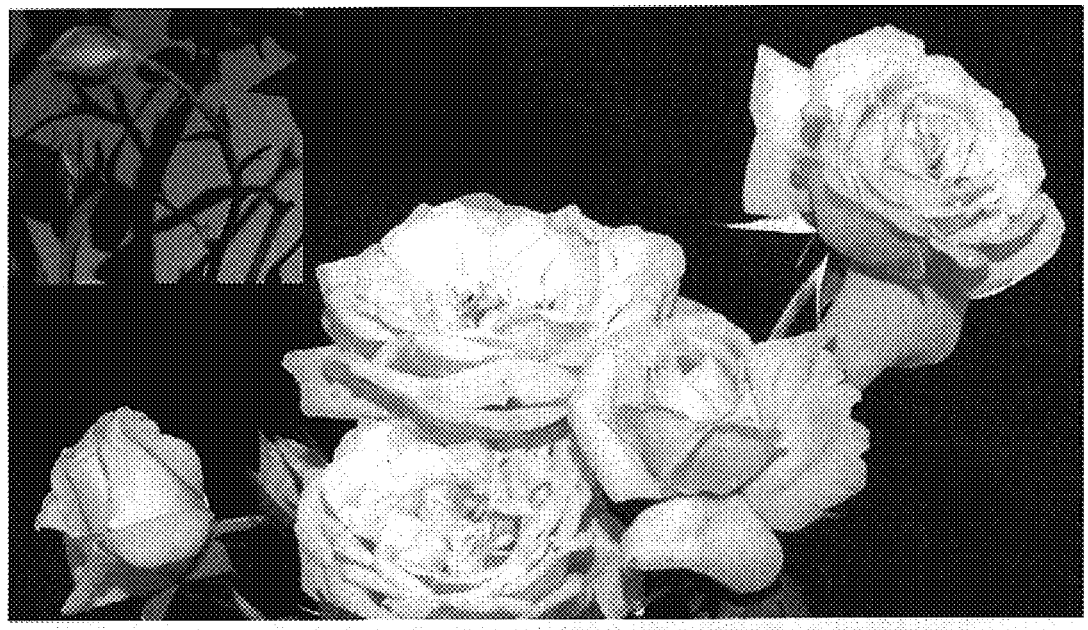
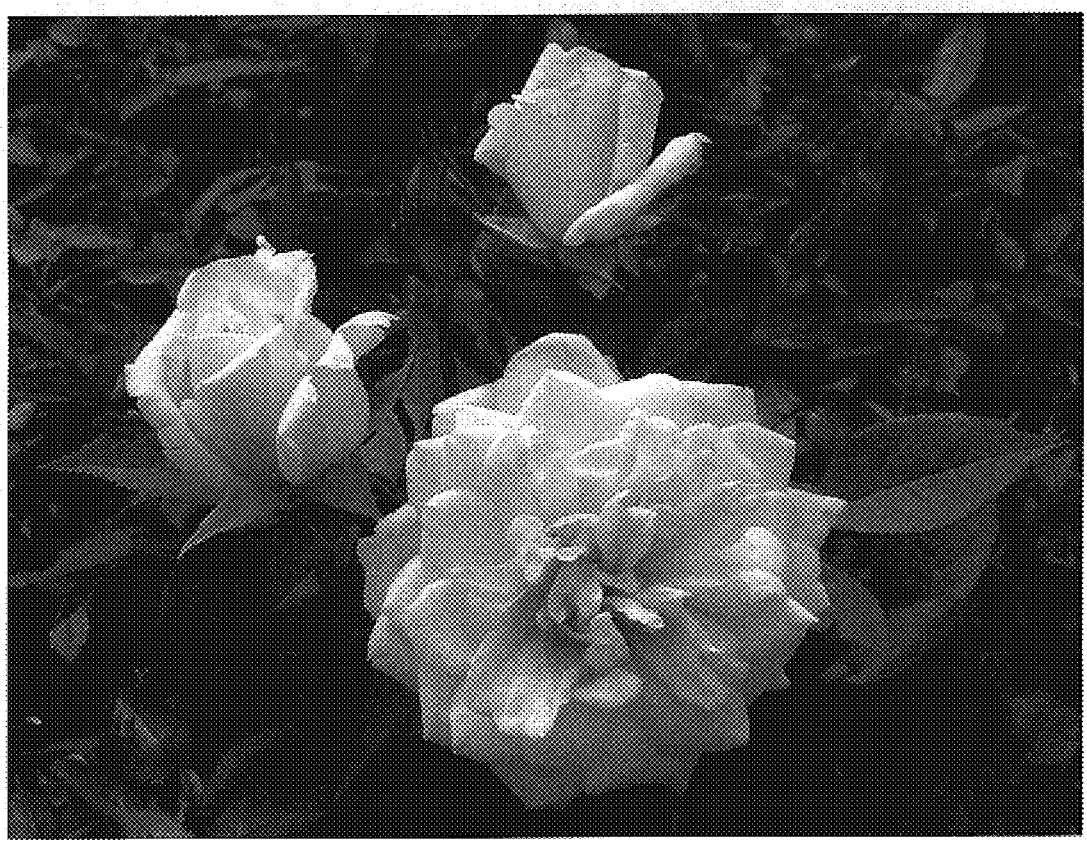

* * * * *